(12) United States Patent
Wen et al.

(10) Patent No.: US 12,303,162 B2
(45) Date of Patent: May 20, 2025

(54) NEEDLE GUIDE FOR AN ANGLED ENDOCAVITY TRANSDUCER

(71) Applicant: EXACT IMAGING INC., Markham (CA)

(72) Inventors: Jerrold Wen, Thornhill (CA); Jerzy A. Smolen, North York (CA); Emma E. Beverly, Mississauga (CA); Craig J. Cermak, Riverside, IA (US)

(73) Assignee: EXACT IMAGING INC., Ontario (CA)

( * ) Notice: Subject to any disclaimer, the term of this patent is extended or adjusted under 35 U.S.C. 154(b) by 683 days.

(21) Appl. No.: 17/437,443

(22) PCT Filed: Mar. 13, 2020

(86) PCT No.: PCT/CA2020/050339
§ 371 (c)(1),
(2) Date: Sep. 9, 2021

(87) PCT Pub. No.: WO2020/181388
PCT Pub. Date: Sep. 17, 2020

(65) Prior Publication Data
US 2022/0168012 A1    Jun. 2, 2022

Related U.S. Application Data

(60) Provisional application No. 62/817,684, filed on Mar. 13, 2019.

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/12* (2013.01);
(Continued)

(58) Field of Classification Search
CPC ..... A61B 17/3403; A61B 8/0841; A61B 8/12; A61B 8/4444; A61B 8/4483;
(Continued)

(56) References Cited

U.S. PATENT DOCUMENTS

| 5,494,039 A | 2/1996 | Onik et al. |
| 6,203,499 B1 | 3/2001 | Imling et al. |

(Continued)

FOREIGN PATENT DOCUMENTS

| JP | 2015521932 A | 8/2015 |
| JP | 7440527 B2 | 2/2024 |

(Continued)

OTHER PUBLICATIONS

International Patent Application No. PCT/CA2020/050339; Int'l Written Opinion and Search Report; dated May 25, 2020; 9 pages.

(Continued)

*Primary Examiner* — Christopher L Cook
(74) *Attorney, Agent, or Firm* — Tarolli, Sundheim, Covell & Tummino LLP

(57) ABSTRACT

A needle guide for an angled ultrasound probe having a port tower with a plurality of needle ports aligned with an angled ultrasonic imaging plane. The needle ports in a port tower are aligned at the offset angle of the angled ultrasound probe and can support and guide a needle at the offset angle. Adjustment of the port tower along the transducer axis of the angled ultrasound probe maintains the alignment of the needle ports relative to the ultrasonic imaging plane and provides adjustment to accommodate differently sized patients. A method is also provided to securely align a needle with an angled ultrasonic imaging plane with an angled ultrasound probe such that the needle can accurately transect the ultrasound imaging plane.

20 Claims, 10 Drawing Sheets

(51) Int. Cl.
*A61B 8/08* (2006.01)
*A61B 8/12* (2006.01)
*A61B 17/00* (2006.01)

(52) U.S. Cl.
CPC .......... *A61B 8/4444* (2013.01); *A61B 8/4483* (2013.01); *A61B 2017/00274* (2013.01); *A61B 2017/3411* (2013.01); *A61B 2017/3413* (2013.01)

(58) Field of Classification Search
CPC .. A61B 2017/00274; A61B 2017/3411; A61B 2017/3413; A61B 10/0241
See application file for complete search history.

(56) References Cited

U.S. PATENT DOCUMENTS

| | | |
|---|---|---|
| 6,206,832 B1 | 3/2001 | Downey et al. |
| 6,398,711 B1 | 6/2002 | Green et al. |
| 9,113,825 B2 | 8/2015 | Chaggares |
| 9,320,494 B2 | 4/2016 | Strong |
| 9,913,596 B2 | 3/2018 | Krieger et al. |
| 2012/0165679 A1 | 6/2012 | Orome et al. |
| 2014/0018667 A1* | 1/2014 | Chaggares ........... A61B 8/4494 600/424 |
| 2015/0366544 A1 | 12/2015 | Yap et al. |
| 2016/0022309 A1* | 1/2016 | Allaway ................ A61B 8/12 600/464 |
| 2016/0338675 A1 | 11/2016 | Kubota |
| 2017/0020558 A1* | 1/2017 | Xu ........................ A61B 8/483 |
| 2018/0116630 A1 | 5/2018 | Dykes et al. |
| 2019/0175214 A1* | 6/2019 | Wood ................ A61B 17/3403 |

FOREIGN PATENT DOCUMENTS

| | | | |
|---|---|---|---|
| WO | 2014009810 A2 | 1/2014 | |
| WO | WO-2016135596 A1 * | 9/2016 | ....... A61B 17/00234 |
| WO | WO 2018/022979 A1 | 2/2018 | |
| WO | 2018167002 A1 | 9/2018 | |

OTHER PUBLICATIONS

JP Office Action for JP Patent Application No. 2021-553861, dated Sep. 26, 2023, 4 pgs.
JP Notice of Allowance for JP Patent Application No. 2021-553861, dispatch date Jan. 30, 2024, 3 pgs.
JP Notice of Allowance for JP Patent Application No. 2021-553861, dispatch date Jan. 30, 2024, 1 pg.
JP Office Action for corresponding JP Patent Application No. 2021-553861, dated Sep. 26, 2023, 2 pgs.
CN Office Action and Search Report for corresponding CN Patent Application No. 202080020443.0, dated Jan. 31, 2024, 8 pgs.
Extended European Search Report (EESR) for corresponding EP Application No. 20769933.1, dated Oct. 17, 2022, 8 pgs.

* cited by examiner tilt             rotate           pull-out

NEEDLE GUIDE FOR AN ANGLED
ENDOCAVITY TRANSDUCER

CROSS-REFERENCE TO RELATED
APPLICATIONS

This application is the National Stage of International Patent Application No. PCT/CA2020/050339, filed Mar. 13, 2020, which claims the benefit of U.S. Provisional Patent Application No. 62/817,684, filed Mar. 13, 2019, the disclosures of which are incorporated herein by reference in their entireties.

FIELD OF THE INVENTION

The present invention pertains to an ultrasound needle guide for an angled endocavity ultrasound transducer. The present invention also pertains to a tower needle guide for aligning a needle with the transducer window of an angled side-fire endocavity ultrasound transducer.

BACKGROUND

Improving the detection, diagnosis, and treatment of cancer is a significant challenge. Imaging solutions capable of guiding targeted biopsies can improve and accelerate detection and therefore health outcomes for patients. In particular, being able to image and target an area of suspicious tissue for biopsy can allow clinicians to obtain an accurate sample of a region of interest for rapid and early diagnosis. In endocavity ultrasound, an endocavity transducer diagnostic is inserted into a body cavity to examine, image, or biopsy an organ or other body structure. For biopsy, a needle guide is used to guide the biopsy needle to the region of interest while the ultrasound images the biopsy procedure and assists the clinician to navigate the biopsy needle to a desired location within the image and into an intra-cavity bodily structure.

High-frequency ultrasound is a rapidly developing field which uses higher frequencies (>15 MHz) than standard ultrasound and offers a non-invasive means to investigate tissue at the microscopic level with resolutions often better than 100 µm. High-frequency ultrasound is currently used for ophthalmologic, dermatologic, intravascular, as well as internal organ imaging such as prostate and gynecological imaging. High frequency ultrasound can also be used to visualize suspicious regions and target biopsies in real-time and to quickly identify benign or suspicious regions and target biopsies. When used in combination with needle biopsy, high frequency ultrasound can be used to effectively locate and obtain a sample in an area of interest, however alignment of the needle within the high resolution image plane is critical to accurate selection of the biopsy target. In ultrasound and high frequency ultrasound in particular, aligning the biopsy needle in the image plane of the ultrasound image assists in accurately obtaining the biopsy. In particular, the biopsy needle should travel, as accurately as possible, parallel to and intersect with or transect the ultrasound image plane. Angled transducer probes comprise of an ultrasonic transducer array disposed at the end of the transducer such that the transducer array and transducer window is angled with respect to the longitudinal axis of the probe housing. Angled endocavity transducer probes are particularly useful where the location of the organ to be visualized is not easily accessible to ultrasound at an angle parallel to the transducer axis and for easier application of pressure on the organ. However angled endocavity ultrasound transducer probes present a challenge in that the needle needs to be aligned with the visual plane of the ultrasound to accurately visualize the needle path.

In side-fire type angled transducer probes wherein the transducer array is on the side of the transducer rather than the front and the ultrasound image plane is offset from the transducer axis, the biopsy needle alignment can be challenging. One example of an ultrasound probe assembly is described in U.S. Pat. No. 9,113,825 to Chaggares et al., which provides a needle guide alignment feature disposed on an exterior surface of a transducer probe housing such that the needle is aligned in the imaging plane when a protective sheath is disposed between the housing and the needle guide. In this needle guide the needle guide housing is attached to the transducer housing, the needle guide is integrated with the transducer housing, and the needle emerges through the transducer very close to the transducer window and transducer array.

There remains a need for an ultrasound transducer needle guide capable of cooperating with an angled side-fire ultrasound probe. In particular, there remains a need for a needle guide specifically adapted for use with an angled endocavity ultrasound transducer probe to access the prostate through the perineum.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an ultrasound transducer needle guide capable of cooperating with an angled side-fire ultrasound probe. Another object of the invention is to provide a needle guide specifically adapted for use with an angled endocavity ultrasound transducer probe, in particular to access the prostate through the perineum, and a method for using the same with an angled ultrasound transducer.

In an aspect there is provided a needle guide for an angled ultrasound probe having a transducer axis and an angled ultrasonic imaging plane at an offset angle, the needle guide comprising: a port tower comprising a plurality of needle ports, each needle port aligned with the ultrasonic imaging plane; a tower guide coupled to the port tower for adjusting the port tower location along the transducer axis; and a clamp for securing the tower guide to the ultrasound probe, wherein adjustment of the port tower along the transducer axis maintains the alignment of the needle ports to the ultrasonic imaging plane.

In an embodiment of the needle guide, each needle port is aligned at the offset angle and is capable of receiving a needle that transects the ultrasonic imaging plane.

In another embodiment of the needle guide, the needle ports are aligned with the imaging plane in pitch, yaw, or both pitch and yaw.

In another embodiment of the needle guide, the clamp and ultrasound probe comprise complementary mechanical engagement features to allow the clamp and ultrasound probe to releasably mate.

In another embodiment of the needle guide, the tower guide is in sliding engagement with the clamp. In another embodiment, the tower guide and clamp comprise a channel and complementary projection for sliding engagement with the channel. In another embodiment, the clamp comprises at least one channel and the tower guide comprises at least one complementary projection.

In another embodiment of the needle guide, the tower guide and clamp have complementary projections and bores to receive the projections.

In another embodiment of the needle guide, the offset angle of the needle ports is maintained relative to the transducer axis as the tower guide position is moved along the transducer axis.

In another embodiment of the needle guide, the port tower and the tower guide are of a single construction.

In another embodiment of the needle guide, the needle ports are sized to receive a needle of a gauge between about 14 and 22.

In another embodiment of the needle guide, the port tower comprises at least two needle ports.

In another embodiment of the needle guide, the offset angle is between about 5 and 55. In another embodiment of the needle guide, the offset angle is between about 5 and 20.

In another embodiment of the needle guide, the needle ports are spaced apart by between 2 mm and 10 mm.

In another embodiment, the needle guide further comprises numerical identifiers corresponding to elevations on the ultrasonic imaging plane.

In another embodiment of the needle guide, the needle ports are maintained at a fixed distance above a transducer window on the ultrasound probe as the tower guide is translated along the transducer axis. In an embodiment, the fixed distance of a lowermost needle port to the transducer window is greater than 3 mm.

In another embodiment of the needle guide, the needle ports are sized to receive a biopsy needle.

In another aspect there is provided a method for aligning a needle with an angled ultrasound transducer window with an offset angle and angled ultrasound imaging plane, the method comprising: selecting a needle port in a needle guide comprising a plurality of needle ports, the plurality of needle ports at varying distances above the ultrasound transducer window; extending a needle through the needle port securely aligned with the ultrasound transducer window; adjusting a distance of the needle port relative to the ultrasound transducer window; and aligning the needle such that it is capable of transecting the ultrasound imaging plane.

In an aspect of the method, the needle is supported by the needle port at the offset angle.

In another aspect of the method, the ultrasound has a frequency of between 5 to 40 MHz.

In another aspect of the method, the needle port positions the needle at least 3 mm away from the transducer window.

In another aspect of the method, on-screen guidance of the ultrasonic imaging plane directs selection of the needle port.

In another aspect of the method, the needle is a biopsy needle.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION OF THE INVENTION

Figure 1:
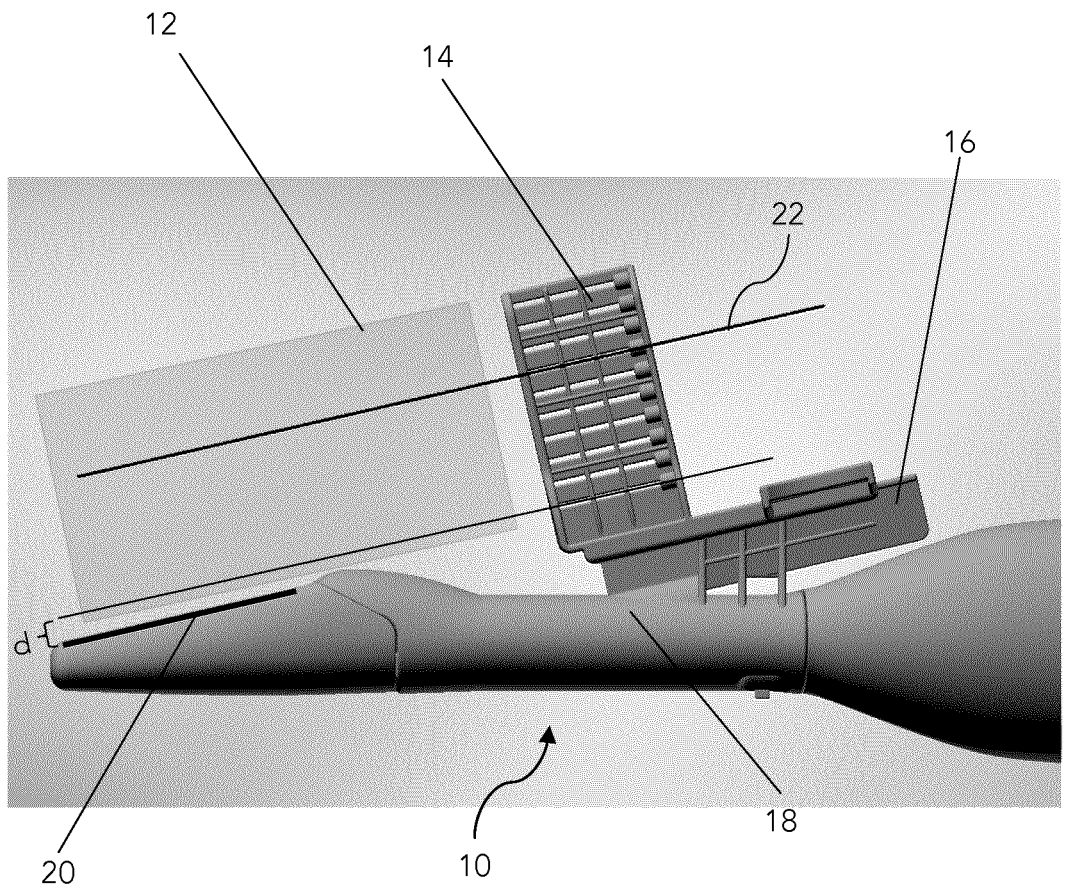
FIG. 1 illustrates an angled endocavity ultrasound transducer with an angled tower guide.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The term "side-fire transducer" refers to an ultrasound transducer probe wherein the transducer transmits ultrasonic waves from a side-wall of the transducer housing. A side-fire transducer can also be thought of as an ultrasound transducer whose transducer array and window are on the side of the probe. Side-fire ultrasound transducers are used particularly in endocavity ultrasound such as for transrectal prostate and gynecological ultrasound.

The terms "angled transducer probe" and "angled ultrasound transducer" as used herein refers to a side-fire ultrasound transducer probe wherein the transducer window of the ultrasound probe is at an angle offset from the transducer probe axis of rotation. Angled transducer probes are particularly useful in endocavity ultrasound where the location of the organ to be visualized is not easily accessible to ultrasound at an angle parallel to the transducer axis. Angled transducer probes comprise an ultrasonic transducer array disposed on the side and end of the transducer such that the transducer array is angled with respect to the longitudinal axis of the probe housing and the image plane is offset from the transducer axis.

Herein is described a tower needle guide for an angled endocavity ultrasound transducer. The presently described needle guide is particularly designed for angled endocavity ultrasound transducers wherein the transducer array, or ultrasound imaging surface and lens, is at an angle relative to the transducer axis. The herein described needle guide is capable of positioning a biopsy needle such that it is aligned with the image plane of the ultrasound providing an accurate guide to simultaneously visualize and biopsy areas of interest in internal structures. The presently described needle guide can also be used for any image guided needle procedure. In one example of an image-guided needle procedure, the present needle guide can be used for targeting treatment of the prostate with needle-assisted therapy delivery, in cases of both cancer or benign growth. The needle guide can thereby be used to accurately apply treatment to locations within organs under ultrasonic image guidance. Examples of treatment include but are not limited to brachytherapy, radiation therapy, cryotherapy, laser ablation, irreversible electroporation, targeted drug therapy, and steam therapy.

The presently described tower needle guide aligns a needle in a position away from or above the ultrasound transducer and at the same angle such that the needle is aligned with and will transect the ultrasound image plane during real time ultrasound imaging. Because the needle is stabilized through a needle port or channel in the tower and distanced from the transducer housing, a broader range of heights away from the transducer window are available for biopsy or needle-assisted therapy. In high frequency ultrasound applications, this provides the clinician with both high resolution imaging of internal organs and structures and simultaneously allows for accurate positioning, securing, and aiming of the biopsy needle into areas of interest. The externally supported tower guide on the transducer housing further allows for a limited range of distances from the transducer window that stabilizes the needle and therefore provide flexibility with body habitus. The needle guide can be used for a variety of medical procedures, such as biopsying organs or other bodily intra-cavity structures, and delivering intra-cavity therapies. The present needle tower guide is particularly useful with a side-fire transrectal imaging probe for prostate imaging, biopsy, and treatment.

FIG. 1 illustrates an angled endocavity ultrasound transducer with an angled needle guide to align a biopsy needle with the ultrasound image plane 12. The proximal section of angled endocavity transducer probe 10 has a proximal end where the transducer probe is inserted into an endocavity, the proximal end having an angled transducer window 20. Port tower 14 has a plurality of stacked needle ports to guide and support a biopsy needle in a range of distances above the transducer window. The lowest positioning of a needle can be achieved using the lowermost needle port in the tower, shown as distance 'd' relative to the transducer window. Tower guide 16 stabilizes the port tower 14 and enables the port tower to be moved toward and away from the proximal end of the transducer probe 10 as required to accommodate each patient while providing a support structure for guiding a needle. Guide clamp 18 secures the tower guide 16 to the transducer probe 10 to stabilize the position of the tower guide device relative to the transducer window 20 to ensure accurate positioning of the biopsy needle 22 during biopsy. The whole device comprising the port tower 14, tower guide 16, and guide clamp 18 can be reversibly attachable to the transducer probe 10 and can be manufactured to be a disposable unit, or one that is capable of being disinfected for multiple uses.

Figure 2:
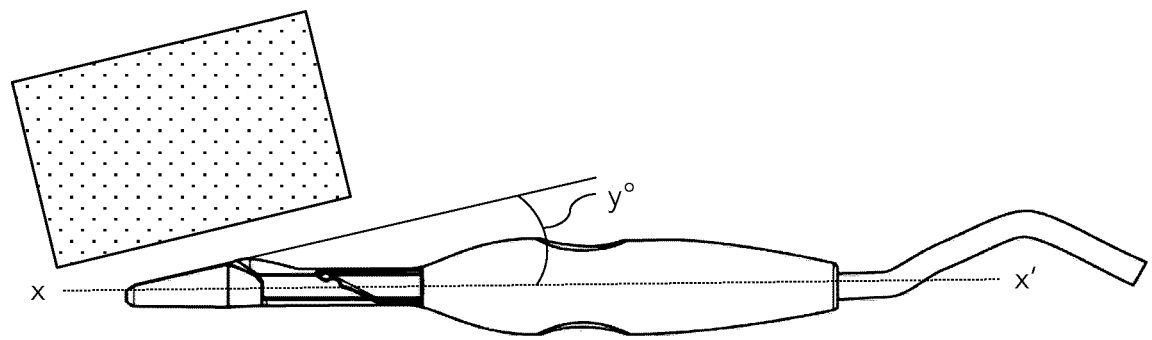
FIG. 2 is an image of an angled side-fire endocavity ultrasound transducer.

FIG. 2 is an image of an angled side-fire endocavity ultrasound transducer. The transducer has a transducer axis of rotation x-x', where x is proximal to the transducer window and x' is distal from the transducer window and at the handle. Angle y° shows the offset angle of the transducer window relative to the transducer axis x-x'. A variety of offset angles, ranging from 5 to 55 degrees, for example, can be envisioned and accommodated with a similar design. Preferably, the offset angle is between about 1° to 30°, with more preferred offset angle between about 5° to 20°, and more preferred offset angle at between about 10° to 15°. In one embodiment, it has been found that a preferable offset angle of 13° can provide improved biopsy needle and imaging access, and easier means of the application of pressure to reduce bleeding and obtain apical samples during biopsy procedure. It is therefore understood that a variety of offset angles can be used and that the angle of the presently described tower guide can be adjusted to match the offset angle of the endocavity ultrasound transducer. In prostate imaging, for example, the prostate is positioned such that an ultrasound probe with angled transducer window projects the ultrasound signal at an anatomically appropriate angle to accurately image the prostate without unnecessary in and out or up and down angle adjustment of the transducer probe when the probe is in the patient. The tower guide provides guidance for a needle during an ultrasound-guided procedure to position the needle relative to the transducer so that the needle image is in a specified position in the ultrasound image during procedures that require precise needle placement.

Figure 3:
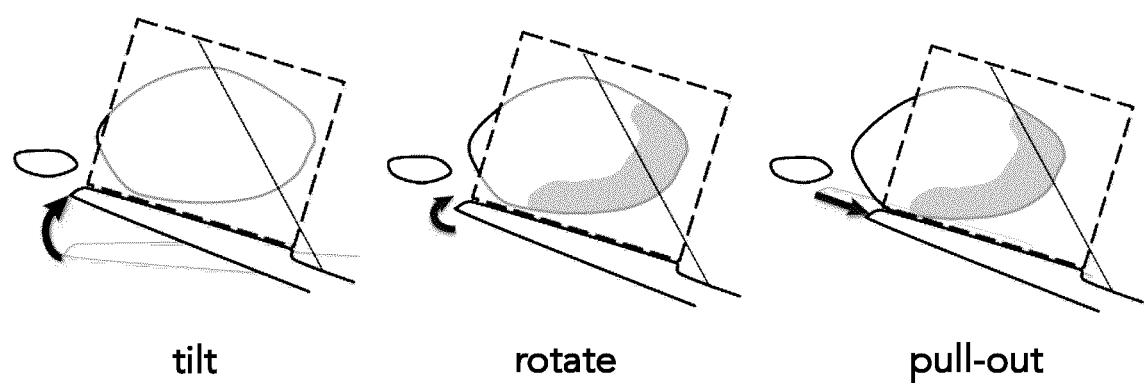
FIG. 3 is an image of a side-fire transducer technique for apical horn sampling.

To view the entire prostate, the offset angle of the angled transducer window allows for tilting the probe to better match the anatomy and manipulate the transducer with minimal movements. FIG. 3 is an image of a side-fire transducer technique for apical horn sampling. In the instance of a transperineal procedure, the transducer is tilted as shown to obtain optimal imaging of the prostate and the angled port tower compensates for the transducer tilt to be flush with the patient's perineum. The transducer can also be rotated to get different cross-sectional views of the organ, and pulled in or out to obtain different views of the organ. In practice, the port tower is positioned at or near the perineum of the patient while still enabling external rotation and positioning of the ultrasound probe, and the port tower can be adjusted along the transducer axis to accommodate the variations in imaging positions required. The adjustable distance of the port tower along the transducer axis x-x' provides a flexible system to adjust to different patient sizes.

The presently described needle tower configuration can be used with high frequency ultrasonic arrays having frequency distributions centered at about 20 MHz or greater, or with ultrasound at any frequency, such as between about 5 MHz to 40 MHz. In one example, the transducer array can be configured to operate at a frequency of 15 MHz or greater, preferably 12 MHz to 29 MHz and is configured to produce a plurality of ultrasonic waves in an ultrasonic imaging plane at an angle offset from the axis of the transducer. The present needle guide can also be used at other ultrasound frequencies, such as from 6-12 MHz, and is not limited to devices operating at higher frequencies. An anatomically compatible housing made with biocompatible material is used to encase the ultrasound transducer probe to improve patient comfort during insertion into the patient.

Figure 4:
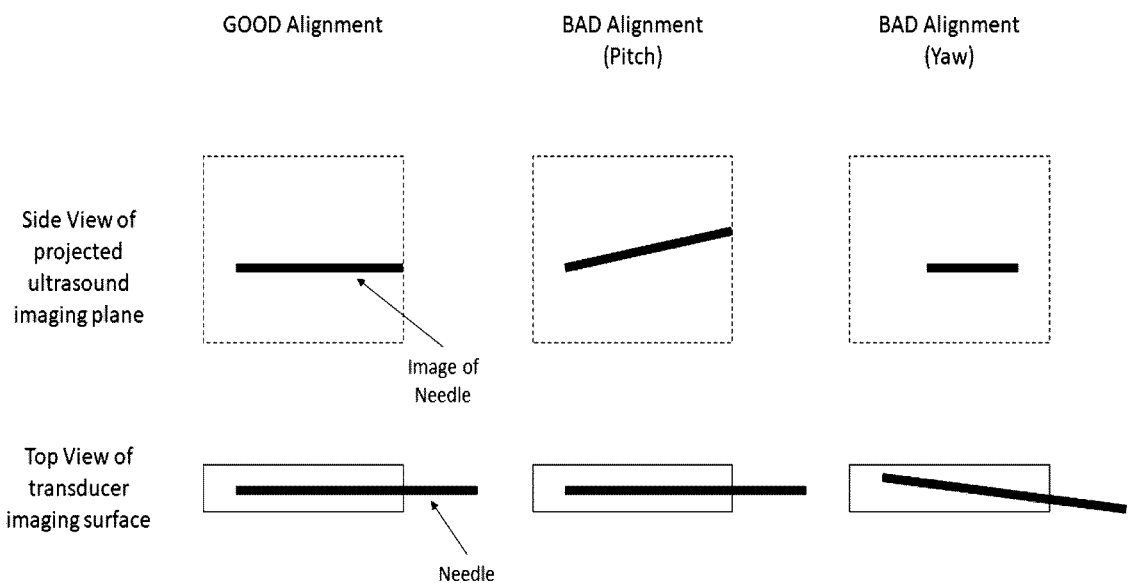
FIG. 4 is an image depicting pitch and yaw needle alignment relative to a transducer imaging plane.

FIG. 4 is an image depicting pitch and yaw needle alignment relative to a transducer imaging plane. The alignment of the needle angle is comprised of the pitch, which is the angle of the needle relative to the transducer window, and yaw, which is the angle of the needle relative to the image plane. As shown, good pitch alignment of the needle means that the needle is substantially parallel to the transducer window and normal to the sides of the ultrasound image. When pitch is off, the angle of the needle is not aligned with the offset angle of the transducer window and the result is that the needle enters the image plane at a non-horizontal angle. Accurate yaw alignment of the needle results in the needle entering the image plane through the plane itself such that the needle barrel enters the organ through the image plane. When yaw is off, the needle barrel transects the image plane and only a fraction of the needle barrel is visible on the image plane. Roll is constrained by the way the tower guide is secured to the guide clamp.

Figure 5:
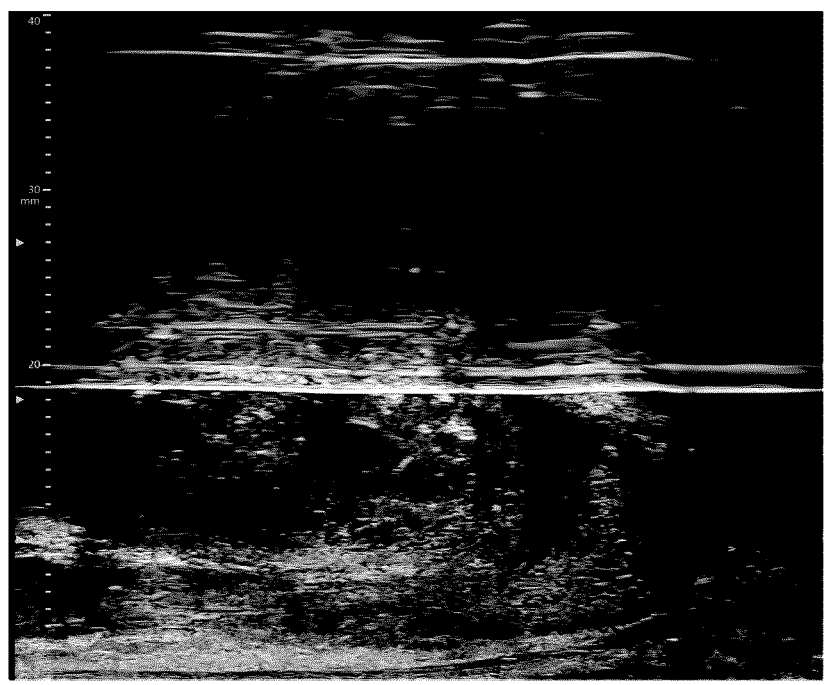
FIG. 5 is an ultrasound image with a biopsy needle guided through a transperineal needle guide.

FIG. 5 is an ultrasound image of a prostate of a suspicious area taken with an endocavity ultrasound transducer using high frequency 29 MHz ultrasound. The biopsy needle is seen as it passes through the image plane of the ultrasound image. As shown on the left-hand side in FIG. 5, an on-screen needle guide can be provided to assist the clinician in aligning the needle trajectory and providing further image guidance to the clinician. In particular, the scale in mm on the left side of the ultrasound image can be used to aid the clinician to select the appropriate needle port on the port tower for the needle such that the needle is accurately aimed at the target of interest.

Figure 6A:
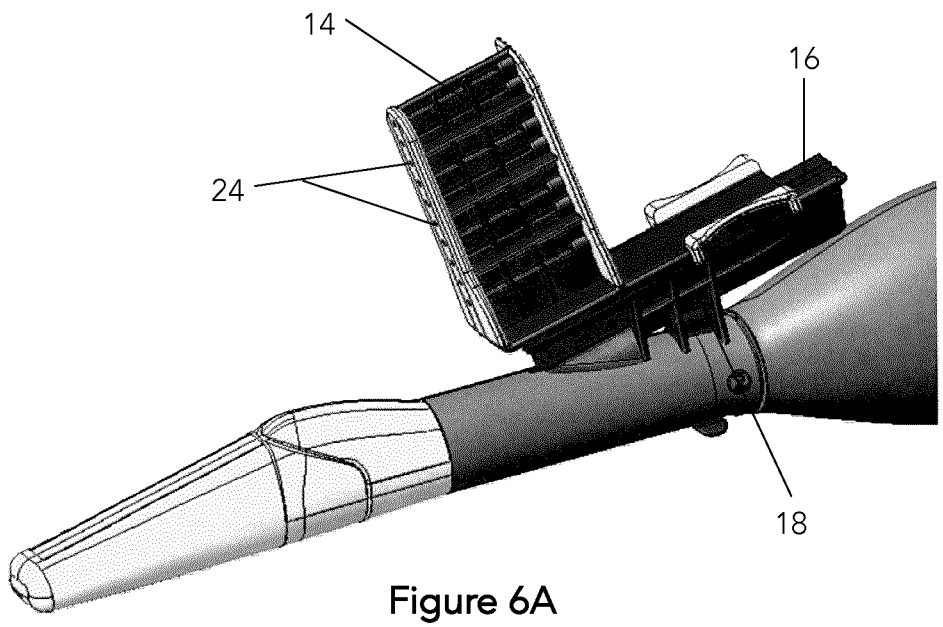
FIG. 6A is a front perspective view of an angled tower guide mounted to an endocavity ultrasound transducer.

FIG. 6A is a front perspective view of an angled needle guide mounted to an endocavity ultrasound transducer. Port tower 14 is supported by and in sliding engagement with tower guide 16, which is secured to the handle of the ultrasound transducer probe through guide clamp 18. The distance of port tower 14 to the transducer window on the ultrasound can be adjusted by sliding port tower 14 along tower guide 16 along the transducer axis. Port tower 14 is angularly aligned with the transducer window of the ultrasound transducer probe, and has a plurality of needle ports 24 which are each angularly aligned with the transducer window. In use, the biopsy needle is guided through the appropriate needle port and should travel as accurately as possible parallel to such that it intersects with and/or transects the edge of the ultrasound image plane. The angle of needle guide thus aligns the biopsy needle parallel to the transducer view window such that it transects the ultrasonic imaging plane and enables detailed visualization in real-time of the prostate anatomy and accurate biopsy of the prostatic tissue of interest. Simultaneous imaging using above conventional ultrasound frequencies provides more image detail and opportunity to visualize suspicious structures of interest earlier. In conjunction with accurate guiding of the biopsy needle this permits navigation of the needle to a specific intra-cavity structure within a human body, or, given sufficient resolution of the ultrasonic transducer, navigation of the needle to a specific location within the structure. Complementary software and on-screen guidance can also assist the user, optionally with an on-screen needle guide adjacent the ultrasound image. This combination of technology can improve the diagnostic capability of the procedure or effectiveness of the delivered therapy.

Port tower 14 is slidable relative to tower guide 16 such that the distance from the proximal or patient side of the port tower 14 and the transducer window on the ultrasound transducer probe can be optimized for varying patient size and shape. As shown, port tower 14 has a platform base that slides along tower guide 16 while maintaining the angle of the needle ports coplanar with the image plane. The travel for the port tower relative to the transducer axis can range from 1-15 cm, and more preferably from 5-9 cm from tower exit port to the edge of the image plane where the needle enters the image. In a device for use in prostate ultrasound, the most proximal positioning of the port tower 14 relative to the transducer window should be the minimal distance for the patients with smallest distance of perineum to prostate, with the sliding port tower 14 capable of accommodating the patients with significantly larger distance from prostate to perineum. The needle guide has adjustable positioning along the transducer shaft or transducer axis, however is positionable with sufficient force or with an optional positioning device to hold the port tower in a secure position. In one example, the target friction force between the port tower 14 and tower guide 16 is in the range of 3±1.0 lb. The needle guide can be continuously or infinitely positionable. In another example, the friction force range may be widened for extended operator usability or for manufacturing yield to 4±2 lbs or 4±3 lbs. Optionally, projection and complementary indentations or notches/stop positions in the port tower or port tower supporting structure and tower guide can provide stop positions to secure the port tower at defined locations relative to the tower guide. Use of the friction based adjustable positioning of the port tower along the transducer shaft at the appropriate offset angle can provide infinite translation range with minimal user manipulation. An alternate embodiment provides a limited number of stops along an infinite translation range. Another embodiment using notches requires a user to detach the tower from its guide and ensure alignment with the image is restored. Further, provided an onscreen needle guide the trajectory of the intersecting needle is continuously visualized in the first embodiment as the tower guide is manipulated, rather than the discontinuity resulting from tower and guide detachment.

Especially in high frequency ultrasound techniques, the port tower should be stable relative to the ultrasound transducer as the high frequency tolerance in image plane is 1 mm in thinnest spot. As such, the needle should be stably guided into the narrow 1 mm image plane. The image plane extends vertically from the transducer window and at a normal to the long axis x-x' of the transducer probe. Because of the high resolution of high frequency ultrasound, mechanical tolerances are much tighter and accuracy and precision more critical. To put this in context, the needle guides needs to provide stability to the needle in the imaging plane. One example needle used with the present needle guide is an 18 gauge needle which is 1.27 mm wide and 20 cm long, with about 10 cm in patient. Other gauges of needle can also be supported by the present needle guide, and the needle ports can be sized and spaced to receive a needle of a gauge, for example, between 14 and 22. The needle ports may also be customized for specific ranges of needle gauges. Typical needle gauges used for ultrasound guided procedures in urology range between 14 and 22 gauge.

The needle ports allow a needle or cannula to pass through the guide paths or needle port with relatively little force, preferably no more than 0.35 lbs. of force. Preferably, the maximum product tolerance of the needle in the needle ports is ±1.0° from the middle of the cannula when measured with an 18 gauge needle device. For example, in a port tower with needle ports sized for 18 gauge needles, the minimum internal diameter of the needle ports is preferably 1.40 mm (0.055 inches). In a port tower sized to receive larger or smaller diameter needles the size of the needle ports should be adjusted to provide the appropriate force and needle tolerance. Shown are ten needle ports 24 on port tower 14, however port tower 14 can have more or fewer. Each needle port should have a length appropriate to stabilize a needle inside the port. Preferably, the needle ports have a length between 20 to 40 mm to balance needle stability and the guide's range of translation. Each of the transperineal needle guide ports in the port tower has a particular spacing, center to center. A scale or ruler on the ultrasound image matching the scale on the needle guide can further provide an indication for the clinician to locate of the tissue of interest. The spacing of the needle ports can range, preferably from 3 mm to 10 mm. In one embodiment each needle port has a 5 mm spacing, though the spacing can be variable. Optionally, each needle port has a countersink on each entrance guide port to facilitate easier needle entry. The materials of the needle guide shall preferably meet the biocompatibility requirements of ISO 10993-1 for externally communicating device, blood path indirect for a limited duration and all features sterilisable. In this particular embodiment, Acrylonitrile Butadiene Styrene (ABS) is used.

Figure 6B:
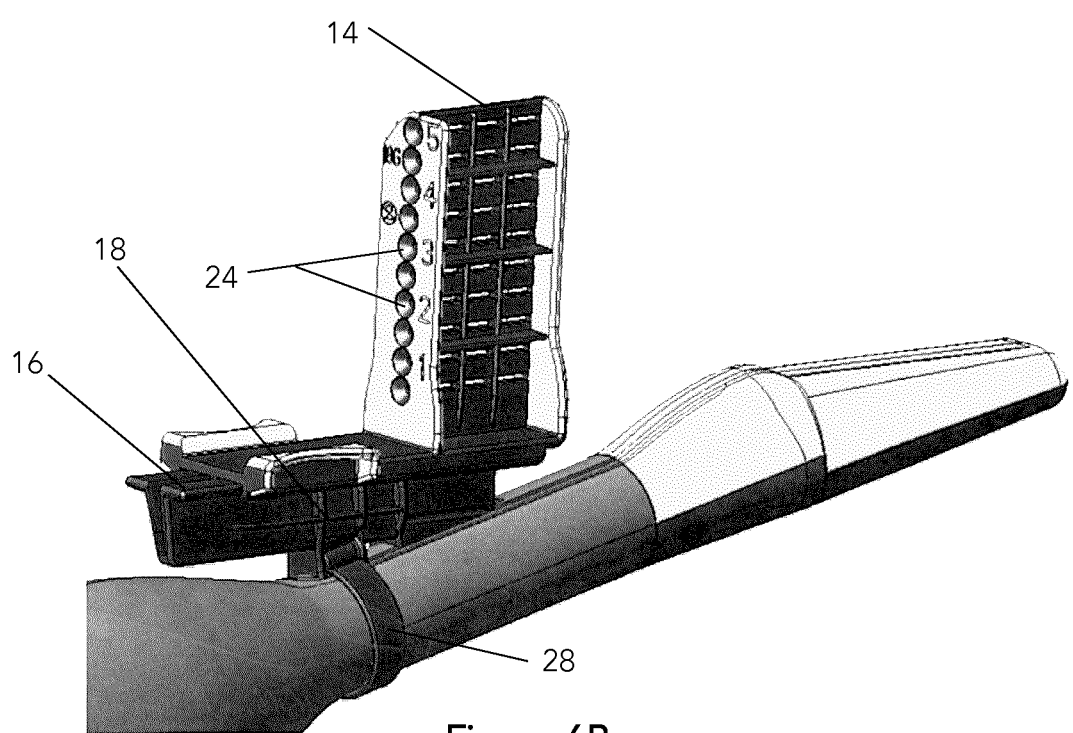
FIG. 6B is a rear perspective view of an angled tower guide for an endocavity ultrasound transducer.

FIG. 6B is a rear perspective view of an angled tower guide for an endocavity ultrasound transducer. The rear view is the view of the clinician when the ultrasound probe is inside the patient. Port tower 14 slides along tower guide 16 and can be adjusted according to the size and shape of the patient. The ultrasound needle guide port tower 14 shown has numerical identifiers (1 to 5) adjacent to every other needle guide port 24 on port tower 14, corresponding to the depth in centimeter starting from the transducer lens. In another embodiment, numerical identifiers can be adjacent to every needle port, with corresponding indicators on the ultrasound image output screen. Preferably the identifiers are high contrast and visible in low light conditions, as ultrasound is often carried out in low light to improve image contrast for the clinician. Guide clamp 18 secures to the ultrasound probe using a latch mechanism 28 which wraps over the exposed transducer and secures over the protrusion on the guide clamp 18. An optional latch mechanism 28 can be friction fitted onto guide clamp 18, and the latch and guide clamp 18 can work in tandem to secure the guide clamp 18 to the transducer housing.

Figure 7A:
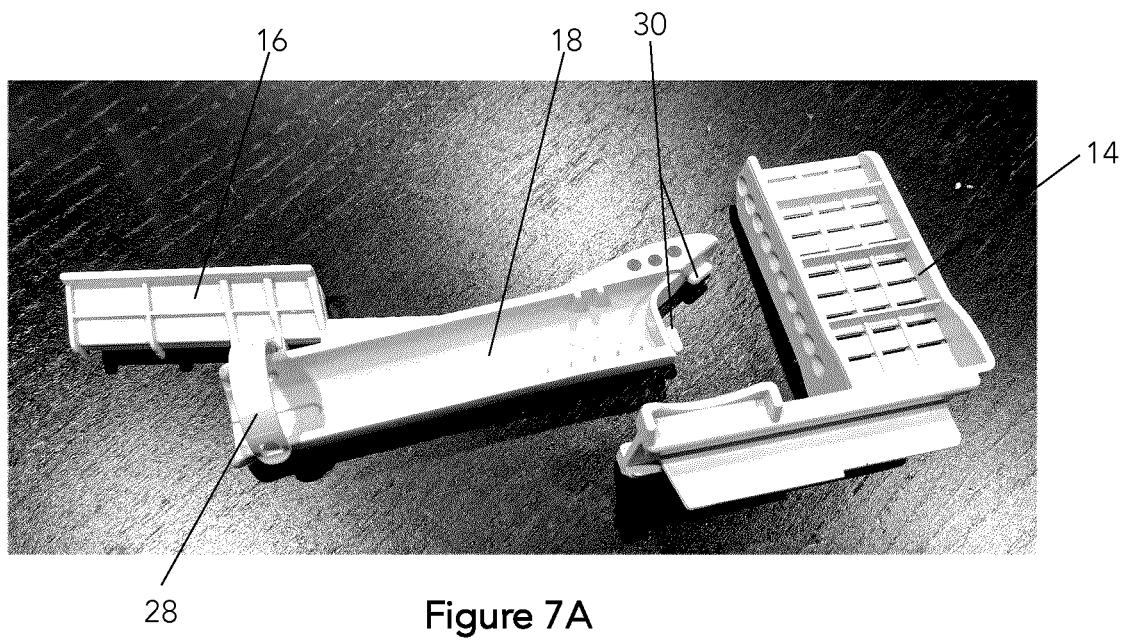
FIG. 7A is a disassembled view of components of an angled needle guide.

FIG. 7A is a disassembled view of components of an angled tower guide. Shown are port tower 14 with a platform having a lower fin or protrusion that fits into a complementary channel in tower guide 16. Latch 28 further secures guide clamp 18 to the ultrasound transducer for a secure fit.

Figure 7B:
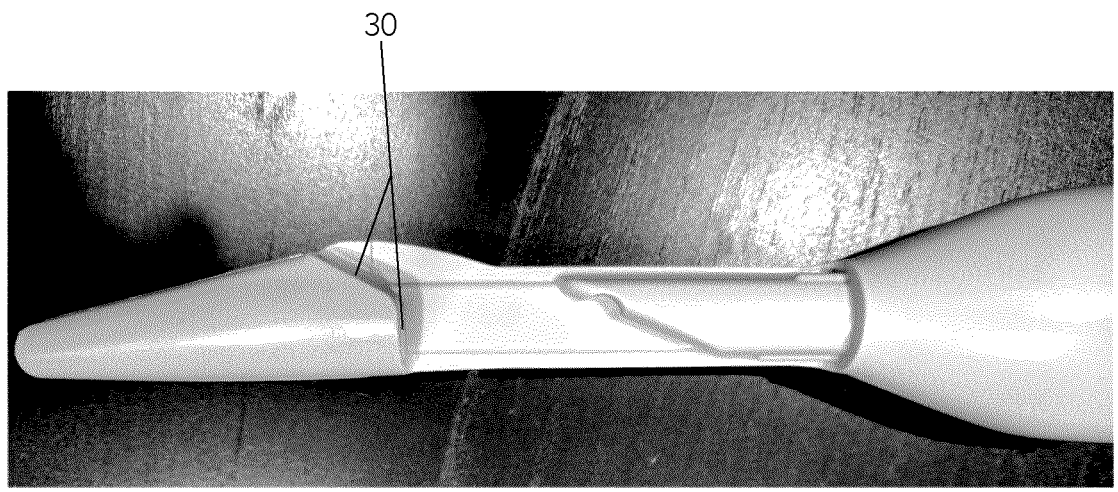
FIG. 7B is a side view of an endocavity ultrasound transducer with a housing for receiving a needle guide.

FIG. 7B is a side view of an endocavity ultrasound transducer with a housing for receiving a needle guide. Port tower 14 slides along tower guide 16. The side of the ultrasound transducer housing is configured such that the guide clamp fits into the side of the housing and is securable using mechanical alignment features but removable from the complementary ultrasound probe housing. Complementary mechanical engagement features 30 can be positioned on the promixal and distal ends of the ultrasound probe housing and guide clamp providing one or more depressions and protrusions that accurately fit into one another. These features are deliberately constructed to provide a smooth mating surface and interference such that a protective sheath (condom) can be placed in between these two parts and not be damaged in the process, being secure but releasable for clamp washing or disposal.

Figure 8:
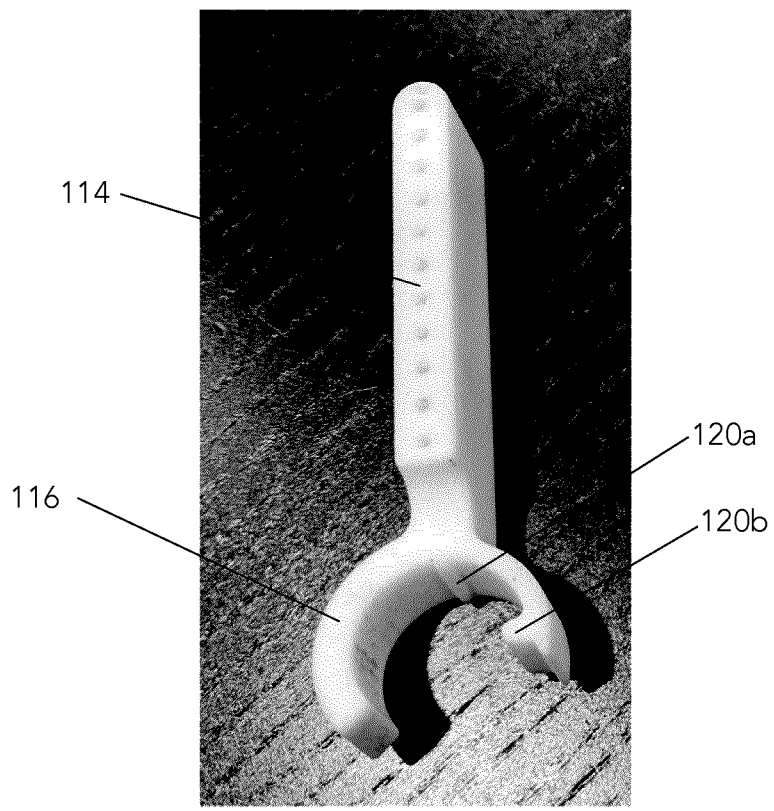
FIG. 8 is a front view of a tower guide.

FIG. 8 is a front view of another embodiment of the tower guide having a port tower 114 and tower guide 116. The tower guide 116 also features two alignment projections 120a, 120b oriented perpendicular to one other that are used for maintaining a friction force between the complementing guide clamp 118 and tower guide 116, and to prevent the port tower 114 from rotating off the guide clamp 118. These tower guide alignment projections also align and allow for continuous positioning of the port tower along a top channel and side channel in the complementing guide clamp (see side channel 122 in FIG. 9A; top channel not shown). Projections do not necessarily need to be perpendicular to one another, nor limited to only two projections. The pitch and yaw of the needle trajectory, as shown in FIG. 4, are controlled by assembly of the two parts, namely the tower guide 116 and clamp which are then constrained together. In this embodiment the port tower and tower guide are fixed relative to one another and rely on the projections for assembly with its complementary channels shown in FIGS. 9A and 9B.

Figure 9A:
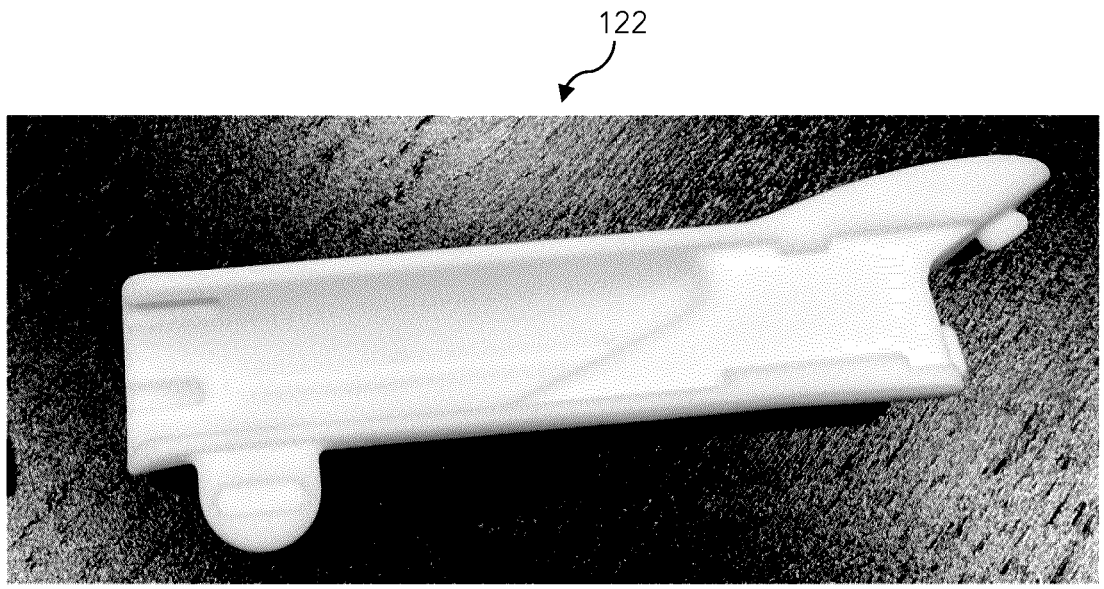
FIG. 9A is an inside side view of a clamp for a needle guide.
Figure 9B:
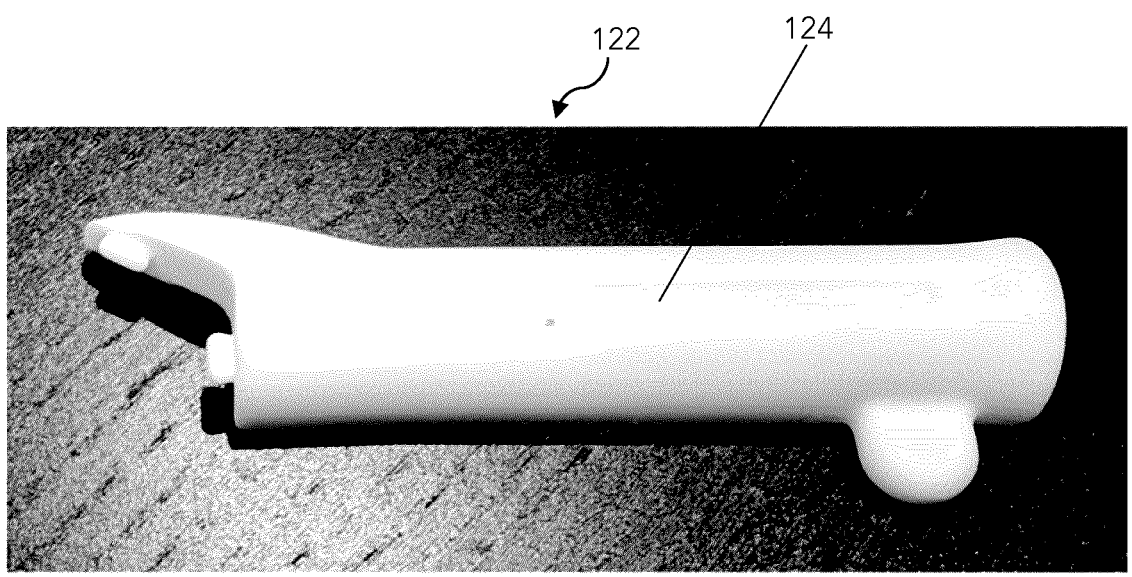
FIG. 9B is an outside side view of a clamp for a needle guide.

FIG. 9A is an inside side view of a guide clamp 122 for the tower guide shown in FIG. 8, and FIG. 9B is an outside side view of the same guide clamp 122. In this embodiment, the outside surface of the guide clamp 122 shown provides two perpendicularly oriented slots running parallel to the transducer axis of rotation that are used to receive the protrusions of the tower guide 116. The protrusions do not necessary need to be perpendicular to one another nor limited to only two, and the guide clamp can comprise, for example, a single channel and associated guide feature. The assembly of this guide clamp 122 with its complementing port tower and tower guide shown in FIG. 8 allows for infinite positioning or continuous movement of the tower along the transducer in a sliding engagement.

Figure 10A:
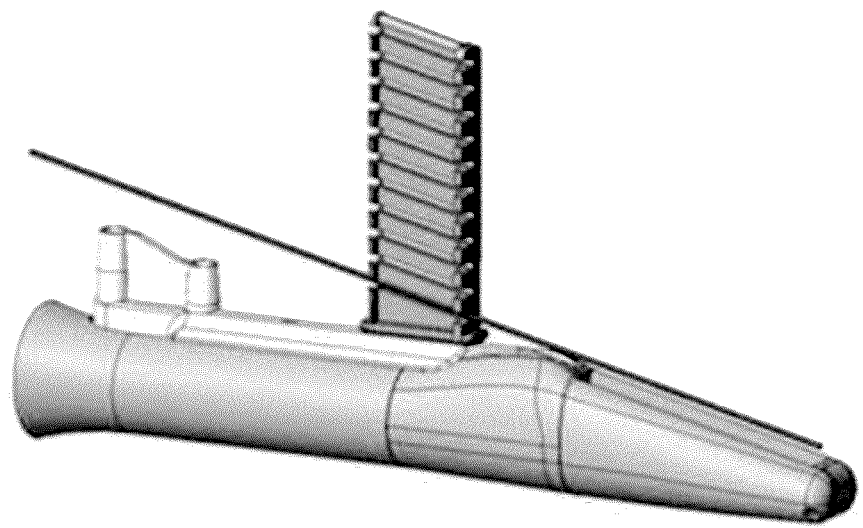
FIG. 10A is a side perspective view of an angled endocavity ultrasound transducer with an angled needle guide in a proximal position.
Figure 10B:
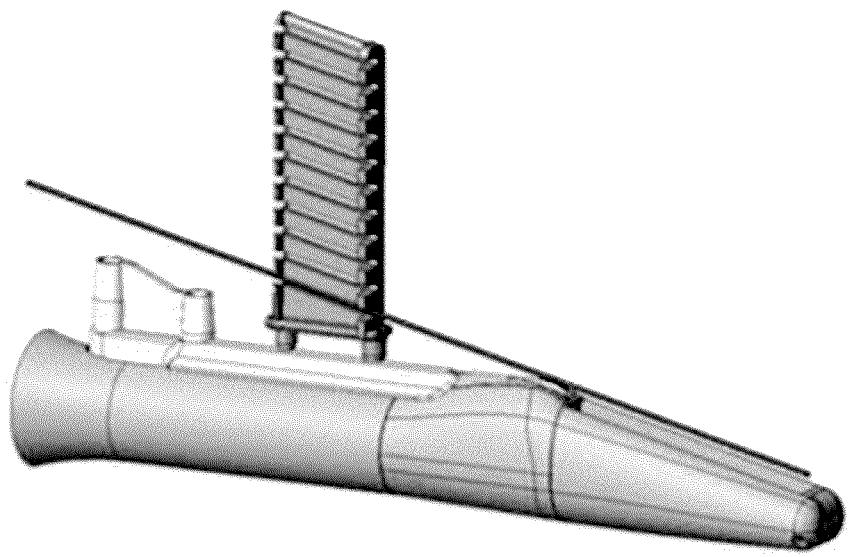
FIG. 10B is a side perspective view of an angled endocavity ultrasound transducer with an angled needle guide in a middle position.
Figure 10C:
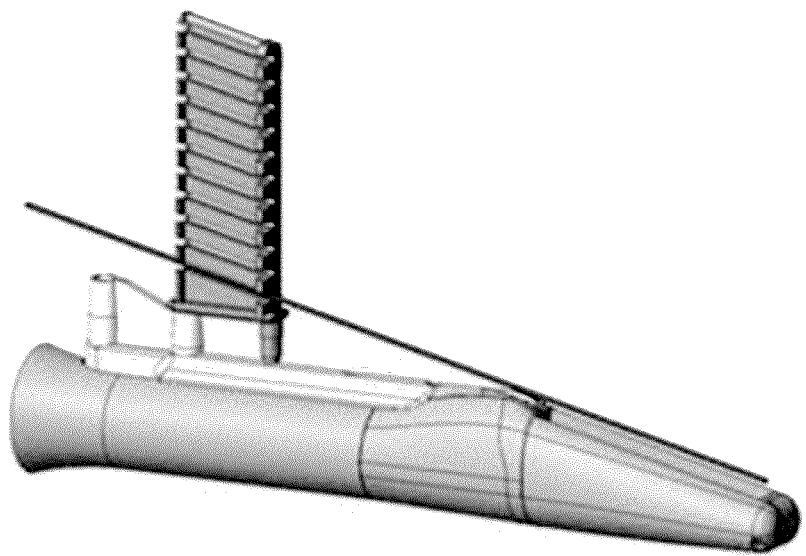
FIG. 10C is a side perspective view of an angled endocavity ultrasound transducer with an angled needle guide in a middle position.
Figure 10D:
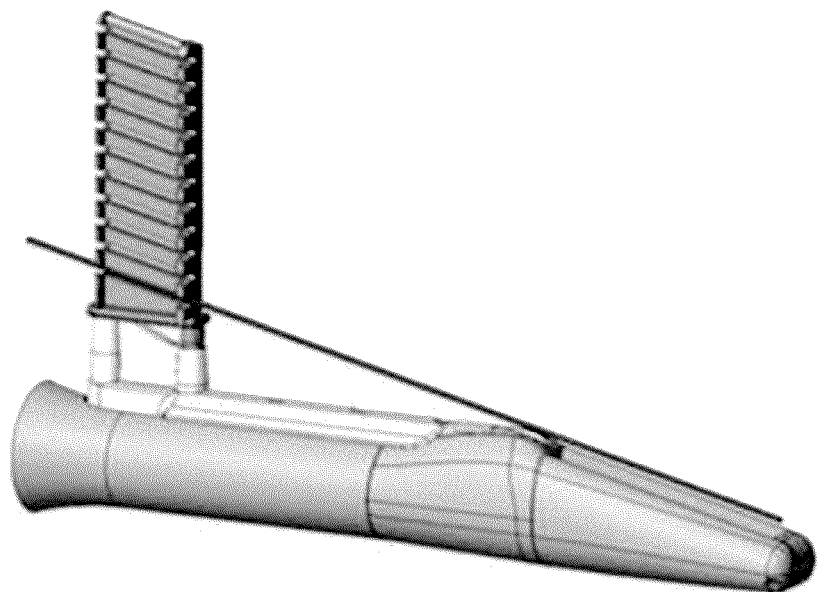
FIG. 10D is a side perspective view of an angled endocavity ultrasound transducer with an angled needle guide in a distal position.

FIGS. 10A-10D show an alternative embodiment of a needle guide wherein the clamp guide and tower guide have complementary pegs and holes for securing the port tower to the clamp guide along the transducer axis. FIG. 10A is a side perspective view of an angled endocavity ultrasound transducer with an angled needle guide in a proximal position relative to the transducer window. FIGS. 10B and 10C are side perspective views of an angled endocavity ultrasound transducer with an angled needle guide in a middle position relative to the transducer window. FIG. 10D is a side perspective view of an angled endocavity ultrasound transducer with an angled needle guide in a distal position relative to the transducer window.

The following clauses are offered as further description of the examples of the apparatus. Any one or more of the following clauses may be combinable with any another one or more of the following clauses and/or with any subsection or a portion or portions of any other clause and/or combination and permutation of clauses. Any one of the following clauses may stand on its own merit without having to be combined with any other clause or any portion of any other clause, etc. Clause 1: A needle guide for an angled ultrasound probe having a transducer axis and an angled ultrasonic imaging plane at an offset angle, the needle guide comprising: a port tower comprising a plurality of needle ports, each needle port aligned with the ultrasonic imaging plane; a tower guide coupled to the port tower for adjusting the port tower location along the transducer axis; and a clamp for securing the tower guide to the ultrasound probe, wherein adjustment of the port tower along the transducer axis maintains the alignment of the needle ports to the ultrasonic imaging plane. Clause 2: The needle guide of any of the clauses, wherein each needle port is aligned at the offset angle and is capable of receiving a needle that transects the ultrasonic imaging plane. Clause 3: The needle guide of any of the clauses, wherein the needle ports are aligned with the imaging plane in pitch, yaw, or both pitch and yaw. Clause 4: The needle guide of any of the clauses, wherein the clamp and ultrasound probe comprise complementary mechanical engagement features to allow the clamp and ultrasound probe to releasably mate. Clause 5: The needle guide of any of the clauses, wherein the tower guide is in sliding engagement with the clamp. Clause 6: The needle guide of any of the clauses, wherein the tower guide and clamp comprise a channel and complementary projection for sliding engagement with the channel. Clause 7: The needle guide of any of the clauses, wherein the clamp comprises at least one channel and the tower guide comprises at least one complementary projection. Clause 8: The needle guide of any of the clauses, wherein the tower guide and clamp have complementary projections and bores to receive the projections. Clause 9: The needle guide of any of the clauses, wherein the offset angle of the needle ports is maintained relative to the transducer axis as the tower guide position is moved along the transducer axis. Clause 10: The needle guide of any of the clauses, wherein the port tower and the tower guide are of a single construction. Clause 11: The needle guide of any of the clauses, wherein the needle ports are sized to receive a needle of a gauge between 14 and 22. Clause 12: The needle guide of any of the clauses, wherein the port tower comprises at least 2 needle ports. Clause 13: The needle guide of any of the clauses, wherein the offset angle is between about 5° and 55°. Clause 14: The needle guide of any of the clauses, wherein the offset angle is between about 5° and 20°. Clause 15: The needle guide of any of the clauses, wherein the needle ports are spaced apart by between 2 mm and 10 mm. Clause 16: The needle guide of any of the clauses, further comprising numerical identifiers corresponding to elevations on the ultrasonic imaging plane. Clause 17: The needle guide of any of the clauses, wherein the needle ports are maintained at a fixed distance above a transducer window on the ultrasound probe as the tower guide is translated along the transducer axis. Clause 18: The needle guide of any of the clauses, wherein the fixed distance of a lowermost needle port to the transducer window is greater than 3 mm. Clause 19: The needle guide of any of the clauses, wherein the needle ports are sized to receive a biopsy needle. Clause 20: A method for aligning a needle with an angled ultrasound transducer window with an offset angle and angled ultrasound imaging plane, the method comprising: selecting a needle port in a needle guide comprising a plurality of needle ports, the plurality of needle ports at varying distances above the ultrasound transducer window; extending a needle through the needle port securely aligned with the ultrasound transducer window; adjusting a distance of the needle port relative to the ultrasound transducer window; and aligning the needle such that it is capable of transecting the ultrasound imaging plane. Clause 21: The method of any of the clauses, wherein the needle is supported by the needle port at the offset angle. Clause 22: The method of any of the clauses, the ultrasound has a frequency of between 5 to 40 MHz. Clause 23: The method of any of the clauses, wherein the needle port positions the needle at least 3 mm away from the transducer window. Clause 24: The method of any of the clauses, wherein on-screen guidance of the ultrasonic imaging plane directs selection of the needle port. Clause 25: The method of any of the clauses, wherein the needle is a biopsy needle.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

We claim:

1. A needle guide for an angled ultrasound probe having a transducer axis and
    an angled ultrasonic imaging plane at an offset angle that is an acute angle relative to the transducer axis, the needle guide comprising:
    a port tower comprising:
        a plurality of needle ports, each needle port having an offset angle matching the offset angle of the angled ultrasonic imaging plane; and
        a platform base integrated with the plurality of needle ports, the platform base having a protrusion underlying the port tower, wherein the platform base and the port tower form a rigid member; and
    a clamp for securing the tower guide to the ultrasound probe, the clamp comprising a tower guide having a channel for receiving the protrusion of the platform base,
    wherein:
    adjustment of the port tower along the transducer axis maintains the alignment of the needle ports to the angled ultrasonic imaging plane;
    the offset angle of the needle ports is maintained relative to the transducer axis as the port tower position is moved along the transducer axis; and
    the protrusion and the channel enable linear movement of the port tower and the linear movement is parallel to the offset angle of the angled ultrasonic imaging plane.

2. The needle guide of claim 1, wherein each needle port is aligned with the angled ultrasonic imaging plane at the offset angle of the ultrasonic imaging plane and is capable of receiving a needle that transects the ultrasonic imaging plane.

3. The needle guide of claim 1, wherein the needle ports are aligned with the angled ultrasonic imaging plane in pitch, yaw, or both pitch and yaw.

4. The needle guide of claim 1, wherein the clamp and ultrasound probe comprise complementary mechanical engagement features to allow the clamp and ultrasound probe to releasably mate.

5. The needle guide of claim 1, wherein the tower guide is in sliding engagement with the clamp.

6. The needle guide of claim 1, wherein the tower guide and clamp have complementary projections and bores to receive the projections.

7. The needle guide of claim 1, wherein the needle ports are sized to receive a needle of a gauge between 14 and 22.

8. The needle guide of claim 1, wherein the port tower comprises at least 2 needle ports.

9. The needle guide of claim 1, wherein the offset angle of the angled ultrasonic imaging plane is between about 5° and 55°.

10. The needle guide of claim 1, wherein the offset angle of the angled ultrasonic imaging plane is between about 5° and 20°.

11. The needle guide of claim 1, wherein the needle ports are spaced apart by between 2 mm and 10 mm.

12. The needle guide of claim 1, further comprising numerical identifiers corresponding to elevations on the angled ultrasonic imaging plane.

13. The needle guide of claim 1, wherein the needle ports are maintained at a fixed distance above a transducer window on the ultrasound probe as the tower guide is translated along the transducer axis.

14. The needle guide of claim 13, wherein the fixed distance of a lowermost needle port to the transducer window is greater than 3 mm.

15. The needle guide of claim 1, wherein the needle ports are sized to receive a biopsy needle.

16. The needle guide of claim 1, wherein the protrusion of the platform base comprises a first portion having a first width and a second portion having a second width, the second width being greater than the first width, and a length of the first portion defines a range of the linear movement of the port tower.

17. The needle guide of claim 16, wherein the port tower further comprises a handle portion overlaying the second portion of the protrusion, the handle portion comprising a first member and a second member that extend parallel to a top of the platform base, the first member and the second member being spaced apart from the plurality of needle ports.

18. The needle guide of claim 16, wherein the first portion and the second portion of the protrusion of the platform base extend on a same plane as a center the plurality of needle ports of the port tower.

19. The needle guide of claim 1, wherein the port tower, the tower guide and the clamp are disposable.

20. A needle guide for an angled ultrasound probe having a transducer axis and an angled ultrasonic imaging plane at an offset angle that is an acute angle relative to the transducer axis, the needle guide comprising:
- a port tower comprising:
  - a plurality of needle ports, each needle port having an offset angle matching the offset angle of the angled ultrasonic imaging plane; and
  - a platform base integrated with the plurality of needle ports, the platform base having a protrusion underlying the port tower, wherein the platform base and the port tower form a rigid member; and
- a clamp for securing the tower guide to the ultrasound probe, the clamp comprising a tower guide having a channel for receiving the protrusion of the platform base;
- wherein the offset angle of the needle ports is maintained relative to the transducer axis for different positions of the port tower along the channel.

* * * * *